United States Patent [19]

Smith et al.

[11] Patent Number: 4,803,162

[45] Date of Patent: Feb. 7, 1989

[54] COMPOSITION, ARTICLE AND PROCESS FOR DETECTING A MICROORGANISM

[75] Inventors: Robert E. Smith, Livermore; Eugene N. Fox, Kensington, both of Calif.

[73] Assignee: Fluorodiagnostic Limited Partners, Walnut Creek, Calif.

[21] Appl. No.: 610,324

[22] Filed: May 15, 1984

[51] Int. Cl.$^4$ .................. C12Q 1/14; C12Q 1/04; C12Q 1/36; C07D 215/16
[52] U.S. Cl. .................. 435/36; 435/34; 435/24; 435/805; 546/158
[58] Field of Search .......... 435/4, 23, 24, 29, 34, 435/36, 39, 212, 220, 805, 885; 436/169, 172; 422/52, 56; 260/112.5 L; 546/158

[56] References Cited

U.S. PATENT DOCUMENTS

| | | | |
|---|---|---|---|
| 3,733,321 | 5/1973 | Krapcho | 546/158 X |
| 4,258,185 | 3/1981 | Nakao et al. | 546/158 X |
| 4,259,442 | 3/1981 | Gayral | 435/36 |
| 4,277,479 | 7/1981 | Nishi et al. | 546/158 X |
| 4,294,923 | 10/1981 | Smith et al. | 435/23 |
| 4,388,233 | 6/1983 | Bissell et al. | |
| 4,505,852 | 3/1985 | Rasnick et al. | 260/112.5 L |
| 4,593,035 | 6/1986 | Tominaga et al. | 546/158 |

FOREIGN PATENT DOCUMENTS 2068943A 8/1981 United Kingdom ............ 546/158
2140423 11/1984 United Kingdom .

OTHER PUBLICATIONS

Analytab Products, API 20S Streptococcus Product Instructions, 1-81.
API System S.A., Rapid Strep Product Instructions, 3-82.
Facklam et al., Presumptive Identification of Streptococci with a New Test System, 6-82.
Szewczuk and Mulczyk, Pyrrolidonyl Peptidase in Bacteria, 1969.
Chemical Abstracts, vol. 95, 1981, Abstract No. 150,468j.
Chemical Abstracts, vol. 33, 1939, Abstract No. 7797-9.

Primary Examiner—Robert J. Warden
Assistant Examiner—Randall E. Deck
Attorney, Agent, or Firm—Glen R. Grunewald; Thomas R. Lampe

[57] ABSTRACT

A compound for detecting the presence of specific microorganisms wherein the compound is made of two molecule fragments connected with a peptide bond, one compound fragment being enzyme-specific in that the presence of an enzyme specific to the microorganisms being detected will cause the peptide bond to hydrolyze, and the other molecule fragment being 6-aminoquinalone, wherein the organism is detected by exposing the compound to fluid suspected to contain the microorganism and irradiating the thus-exposed compound with ultraviolet radiation whereby fluorescence is observed if the microorganism is present.

16 Claims, No Drawings

COMPOSITION, ARTICLE AND PROCESS FOR DETECTING A MICROORGANISM

FIELD OF THE INVENTION

This invention is in the field of detecting the presence of a microorganism.

BACKGROUND OF THE INVENTION

Detecting the presence of a specific miroorganism is useful as a diagnostic tool as well as for other reasons. In the past mircroorganisms have been detected by growing a colony of them on a suitable medium and then examining the colony microscopically. This method is slow and expensive. In general it must be conducted in a laboratory and it takes several days which makes it unsatisfactory for quick diagnosis, for example, in a physician's office.

Techniques have been developed to detect the presence of specific microorganisms by detecting the presence of enzymes produced by those microorganisms rather than looking for the microorganisms themselves. This technique generally uses a synthetic substrate that reacts in the presence of a microorganism's enzyme to produce a compound that is identified by color or by fluorescence in ultraviolet radiation (UV). U.S. Pat. No. 4,388,233 issued to Bissell et al. is representative of the process employing this technique.

The technique of the Bissell et al patent in general employs a compound having an A portion of molecule fragment and a B portion of molecule fragment connected by a hydrolyzable peptide bond. The A portion is specific to the enzyme to be detected in that the presence of that enzyme will cause the peptide bond to be hydrolyzed to thereby produce two molecules, one of which is made from the A fragment and one of which is made from the B fragment. The B fragment of the molecule has a colorimetric or fluorescent quality that permits detection of the enzyme by observing a color change or fluorescence. Specifically, if the detection compound changes color it is because the microorganism's enzyme was present and the B compound was formed with its characteristic color or fluorescing characteristic. The A portion or fragment of the molecule is enzyme-specific, that is, the A portion or fragment of the molecule will cause it to hydrolyze in the presence of the enzyme of the particular microorganism being detected but will prevent hydrolysis of the peptide link or bond by enzymes other than the one to be detected.

Problems encountered with this method for detecting microorganisms are that sharp, unequivocal results are sometimes difficult to obtain. Known colorimetric and fluorescent tests frequently produce equivocal results in which a color shift must be compared with a standard which frequently requires a subjective determination or fluorescense and is difficult to distinguish from the background or difficult to observe because the visible radiation resulting from fluorescense is too close to the blue spectrum as well as being weak. In many such tests different analysts will reach different conclusions regarding a color change or fluorescence.

SUMMARY OF THE INVENTION

In one aspect, this invention is a compound having an enzyme-specific fragment connected through a peptide bond to yield a compound having the following structure:

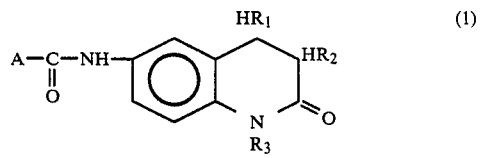

In the structure of compound (1), A is a enzyme-specific substituent and R1, R2 and R3 are independently selected from hydrogen, alkyl groups having fewer than five carbon atoms and haloalkyl groups having fewer than five carbon atoms. When A is a fragment that is enzyme-specific to the enzymes produced by a particular microorganism, in the presence of that enzyme the peptide link will hydrolyze yielding as one of the reaction products the molecule:

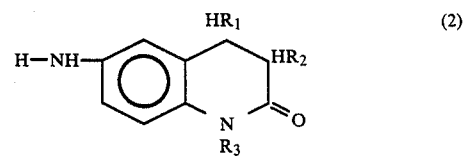

This compound is 6-aminoquinalone, which will hereinafter be referred to as 6AQ. 6AQ is brilliantly fluorescent when irradiated with ultraviolet light so that its presence can be unequivocally detected. In the preferred 6AQ fragment R1, R2 and R3 are all hydrogen however, another preferred 6AQ fragment uses trifluoromethyl in the R1 position and hydrogen in each of the R2 and R3 positions.

In addition to 6AQ being brilliantly fluorescent, the reaction producing 6AQ is normally effected quite rapidly at ordinary conditions of temperature and pressure found in a room. The enzymatic reactions producing 6AQ require no special equipment to create conditions to form the the 6AQ molecule. In addition, the 6AQ molecule fluoresces brilliantly at UV excitation wavelengths in the region of 360nm and inexpensive equipment producing that region of radiation frequencies is very common. Ultraviolet wavelengths between 250nm and 400nm are useful to produce fluorescence of the 6AQ molecule. As will be shown below, a definitive diagnosis can be made in as little as ten minutes using only an inexpensive UV source. As a result a diagnosis can be made in the course of a visit to a physician's office without sending specimens to a laboratory, without requiring secondary visits of followup telephone calls, and most important, a definitive diagnosis made during a visit can result in initiating treatment of the patient immediately.

The invention also encompasses articles of manufacture. These articles are the composition of structure (1) impregnated in dry form into a neutal absorbing medium. A neutral absorbing medium typically is filter paper although it may include such materials as porous minerals such as silica, alumina, and Bentonite, or it may employ poous organic materials such as polystyrene, polyethylene, cellulose hydrate and cellulose acetates. The porous mineral and organic materials may either be in the form of small beads or pellets or they may be in the form of films supported on glass slides or the like. A porous, neutral medium impregnated with a composition of structure (1) has substantially indefinite shelf life when stored at reasonable conditions of temperature and humidity. They occupy a very small amount of space and are suitable for being shipped and stored. An additional advantage of the composition and the articles of this invention is that when a test to detect the presence of a microorganism is made, in the presence of water, the article of this invention may then be dried and the stable 6AQ reaction product resulting from the test becomes impregnated into the article of this invention so that the test may be stored in the file of the patient and may be retrieved and reexamined any time in the future whereupon irradiating it with ultraviolet light will show the exact location and pattern of fluorescense as was shown when the test specimen was originally made. The dried test specimens may also be shipped to different locations so that they can conveniently be examined by other analysts.

The articles of this invention are preferably made of absorbent papers such as filter paper and are preferably mounted much as 35mm slides are mounted so that the test results may be kept without danger of being destroyed. The articles are used by applying to the portion of it that's impregnated with the composition of structure (1) a small specimen of body fluid suspected of containing the microorganisms. Typically, one suspected of having a streptococcus infection would have a fluid sample taken from his throat with a swab and have a portion of that fluid sample applied to the dried article impregnated with a compound having an A fragment specific to streptococcus. The dried article is then moistened with water, preferably containing a suitable buffer to establish pH suitable to promote enzyme activity, after which enough time is perrmitted to elapse for the chemical reaction to be effected and then the article is exposed to ultraviolet radiation. A pH of between 6 and 9 is preferred to promote the reaction. If brilliant yellow-green fluorescence is observed the presence of the streptococcus infection is confirmed and if no fluorescence is observed the test is negative and no streptococcus is present in the patient's throat.

As with all chemical reactions the hydrolysis of the structure (1) composition is promoted by higher temperatures. The reaction also must take place in the presence of water. Thus, after a body fluid is applied to a test strip and the buffer solution is applied to the test strip, the test strip advantageously is inserted into a plastic envelope to prevent too rapid evaporation of water. The reaction is accelerated when the test strip is incubated to about 35° C. Tests conducted under these conditions normally yield a confirming result within 10 minutes.

It has also been found that if a test specimen is maintained wet too long the 6AQ formed from the enzyme promoted reaction product will become dispersed throughout the test strip. Accordingly, it is preferred to conduct all tests in a manner such that the water from the buffer solution will evaporate in about 30 to 60 minutes. When the water has evaporated the result of the test is captured within the absorbent medium where it can remain indefinitely as set forth above. Therefore, sealing a test strip within a plastic envelope is not a preferred way to conduct a test but rather placing it in a plastic envelope that is provided with ventilation, preferably byleaving an open end, to effect drying within a reasonable time is preferred. A plastic envelope used for this purpose, of course, should not fluoresce in the presence of ultraviolet and it should be neutral with respect to all of the reactants employed in the process.

It is evident that drying time is also influenced by temperature, humidity, and the amount of water applied to the specimen in the first place. Drying time is not critical because the degree of diffusion of the 6AQ throughout the test strip is continuous. Conditions should be used to maintain the test strip wet only long enough to insure adequate reaction time. Wide latitude is available for obtaining satisfacotry results with any particular absorbent medium, buffer solution, or ambient conditions within the testing area.

Some specific compositions are more useful than others within the broad scope of this invention. It has been found that when R1, R2, and R3 are alkyl groups the wavelengths of visible light resulting from fluorescence will be shifted toward blue and will not be as brilliant as when R1, R2 and R3 are hydrogen. When R1, R2 and R3 are hydrogen a brilliant yellow-green fluorescence is obtained that not only is readily discernible but which even sharply outlines those areas of the test strip where the suspected body fluid was applied. R1, R2 and R3 should not contain oxygen, sulphur or nitrogen within their structures but halogen containing groups both fluoresce strongly and produce visible light toward the red spectrum which makes the fluorescence more brilliant and which make fluorescence more readily distinguishable.

Although this invention is useful with many A type molecule fragments for detecting the presence of a number of different microorganisms, it is particularly useful in detecting the presence of group A streptococcus. The A fragment of the compound useful to detect group A streptococcus is one having the following structure:

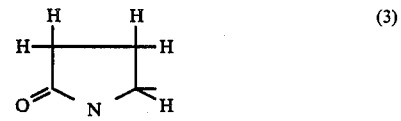

(3)

Thus the preferred composition of this invention is:

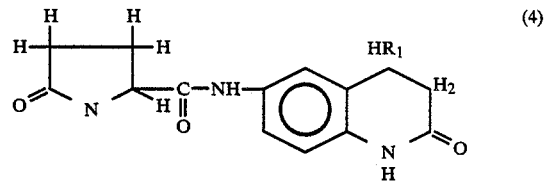

(4)

In which R1 is hydrogen or trifluoromethyl. When R1 is hydrogen, the compound of structure four is pyrrolidonyl-6-aminoquinalone, hereinafter PYR-6AQ.

DETAILED DESCRIPTION OF THE INVENTION

EXAMPLE 1

The compound PYR-6AQ was synthesized by techniques known to the art. The PYR fragment was synthesized enzymatically by internal cyclization of glutamic acid and was esterified by known techniques with 6AQ via a peptide link.

One micromole PYR-6AQ was dissolved in one ml of methanol, and 0.01 ml of the solution was placed in the center of each of a number of one-inch on a side squares of Whatman number 3 filter paper so that a spot at the center of each square approximately ½ inch in diameter was wet. The methanol quickly evaporated leaving a dried residue of PYR-6AQ impregnated into the paper. These test squares were stored and were found to have indefinite shelf life when kept dry and cool.

The throat of a person suspected of having a group A streptococcus infection was swabbed and the fluid from the swab was deposited on the center of the impregnated area of one of the dry test squares. One drop of an aqueous buffer solution was then placed in the center of the test square. The buffer solution was demineralized water having the following ingredients in the noted concentrations:

tris (hydroxymethyl) (amino methane hydrochloride) 0.1M
dithiothretiol (reducing agent) 0.01M
sodium azide (preservative) 0.015M
adjust pH to 6.0 with 1M NaOH and dilute to final volume with water.

The buffer solution includes a reducing agent to maintain sulfur-containing compounds found in many enzymes in the reduced form.

After the buffer was applied the test square was placed in a polyethylene bag approximately 1 inch by 2 inches and an ordinary office staple was placed through the bag and through the test square to hold it in place. The polyethylene bag did not produce fluorescence when exposed to ultraviolet radiation. The end of the polyethylene bag remained open to provide ventilation. The test square fixed in the bag was maintained at room temperature (approximately 70° F.) for twenty minutes and at that time it was still slightly damp but most of the water had evaporated from it.

The test square remained in the bag throughout the entire procedure to be described hereinafter. After the twenty minute interval elapsed the test square was irradiated in a dark room with ultraviolet producing an excitation wavelength of 360nM. Brilliantly fluorescent, yellow-green, irregularly shaped spots were observed on the test square. The position of these spots was where the swab touched the dry test square.

The test square was allowed to dry completely and was stored in a file folder in an ordinary office file drawer. After 180 days it was removed and again subjected to the same ultraviolet radiation and again the same pattern of brilliantly fluorescent, yellow-green areas at the same intensity of the first test were observed. The storage life of the 6AQ in the test square appeared to be indefinite.

EXAMPLE 2

Test squares prepared as set forth in Example 1 were employed in a hospital in the manner set forth in Example 1. Tests were conducted on 110 children and adults suspected of being infected with group A streptococcus. For each patient a conventional lab test for group A streptococcus was also conducted.

Seventeen of the subjects had confirmed group A streptococcal infections by conventional tests and of those thirteen also had positive tests using the test squares. Thus, the positive correspondence of the two test procedures was about 76%. The negative corespondence was about 95%. The statistical significance of these tests is not great. The positive results were based on a sample of only seventeen events and the negative results were based on a sample of only 93 events. Nevertheless, the results are sufficient to demonstrate that the invention using the particular PYR molecule fragment is useful to quickly diagnose group A streptococcus infections. Although it has not been established, it is thought that the failure to produce 100% correspondence between the conventional tests and the tests using the PYR-6AQ compound was due to the lack of specificity of the PYR molecule fragment. That is, microorganisms other than group A streptococci produced enzymes that caused the PYR-6AQ molecule to hydrolyze.

EXAMPLE 3

Test squares made in accordance with Example 1 were used in a diagnostic laboratory for identifying group A streptoccoccal colonies. The colonies were grown on a standard culture medium by known procedures. Colonies of various microorganisms were easily distinguishable from one another by examining them with the naked eye. Four different types of colonies were observed and serologically identified as groups A, B and C and Others that weren't identified. In all, thrity six test squares were used as set forth in Table 1.

The procedure followed for each square was to remove a specimen of a particular colony with a toothpick being careful to avoid any members of another colony or to pick up any of the culture medium. The paper strip was placed on a clean, dry surface and the specimen was placed in its center and spread to cover two to three square millimeters of the test square. Then, as in Example 1, a drop of buffer solution was placed on the inoculated part of the tests square and the square was then placed in and stapled to a plastic bag. After 15 minutes the test squares were irradiated with UV having a wave length of about 300 nM. The data resulting from these tests are recorded in Table 1.

TABLE 1

| GROUP | NO. TESTED | FLUORESCENCE |
|-------|------------|--------------|
| A     | 15         | 15           |
| B     | 11         | 0            |
| C     | 7          | 0            |
| Other | 3          | 0            |

Example 3 demonstrates that among various streptococci, PYR-6AQ is quite specific to group A. In each of the fifteen tests of group A, the test square produced a brilliant, yellow-green fluorescence.

EXAMPLE 4

Test squares produced in the manner of Example 1 were made but instead of PYR-6AQ the square were impregnated with 1-alanyl-6-aminoquinalone (ALA-6AQ). The structure of ALA-6AQ is

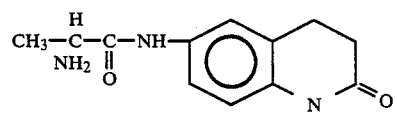

In recent publications it was disclosed that the presence of alanylaminopeptidase in the cell wall of aerobic and facultative anaerobic bacteria correlates with the capacity of those organisms to resist staining by the Gram reagent (see Cerny, G. 1976, *Method for the Distinction of Gram-positive from Gram-negative Bacteria*, Journal of Clinical Microbiology, Vol 16, pp 1157–1159). Bacteria that are Gram-negative react positively to the assay for alanylaminopeptidase while Gram-positive bacteria usually have little or none of this enzyme.

The test squares of this example were prepared by the method of Example 1 using ALA-6AQ instead of PYR-6AQ and for each microorganism named in Table 2 one square was inoculated with a specimen and wet with buffer solution after which the test square was examined under UV light as set forth above. Each microorganism was also assayed with a conventional Gram stain test. The results of these assays are reported in Table 2. In Table 2 the negative test using test squares means that the square did not fluoresce, not that the microorganisms was Gram-negative. In other words, a negative test square indicates a Gram-positive organism.

TABLE 2

| | Gram-Stain Reaction | ALA-6AO TEST |
|---|---|---|
| Gram-Positive Microorganisms | | |
| Staphylococcus aureus | positive | negative |
| Streptococcus pyogenes | positive | negative |
| Corynebacterium diphtheriae | positive | negative |
| Staphylococcus epidermidis | positive | negative |
| Listeria monocytogenes | positive | negative |
| Streptococcus pneumoniae | positive | negative |
| Streptococcus salivarius | positive | negative |
| Bacillus subtilis | positive | negative |
| Grams-Negative Microorganisms | | |
| Shigella flexneri | negative | positive |
| Shigella sonni | negative | positive |
| Edwardsiella tarda | negative | positive |
| Yersinia interocolitica | negative | positive |
| Salmonella cholerasuis | negative | positive |
| Acinetobacter anitratus | negative | positive |
| Salmonella enteriditis | negative | positive |
| Salmonella typimurium | negative | positive |
| Escherichia coli | negative | positive |
| Proteus vulgaris | negative | positive |
| Hemophilus influenzae | negative | positive |
| Hemophilus parainfluenzae | negative | positive |
| Proteus mirabilis | negative | positive |
| Hemophilus hemolyticus | negative | positive |
| Neisseria gonorrhoeae | negative | positive |
| Neisseria meningitidis | negative | positive |

The compound 6AQ can form a peptide bond or link with other enzyme-specific molecule fragments and it is therefore useful for detecting other microorganisms. Specifically, any molecule fragment that is enzyme-specific and which can be esterified via a peptide link to 6AQ may be used in accordance with this invention. It is evident that different substrates may require different aqueous media or other conditions in order to be adapted for testing for the presence of their specific microorganisms but determining such parameters are within the skill of the art.

What is claimed is:

1. A compound having the structure

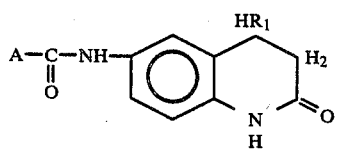

wherein A is an enzyme-specific substituent and R1 is a haloalkyl having fewer than five carbon atoms.

2. The compound of claim 1 wherein R1 is trifluoromethyl.

3. The compound of claim 1 wherein A is

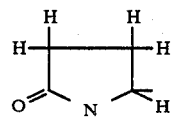

4. The process for detecting the presence of group A streptococci comprising:
  A. bringing a material suspected of containing group A Streptococci into contact with an article comprising the compound of claim 1 impregnated into an absorbent carrier wherein A is a substituent specific to enzymes produced by said group A Streptococci,
  B. moistening said article with an aqueous medium
  C. exposing said article to ultraviolet radiation, and
  D. observing the presence of fluorescence to establish the presence of said group A Streptococci.

5. The process of claim 4 wherein said ultraviolet radiation has a wavelength between 250 and 400nm.

6. The process of claim 4 wherein A is pyrrolidonyl.

7. The process of claim 6 wherein said aqueous medium is water buffered to a pH between 6 and 9.

8. The process of claim 4 wherein said aqueous medium includes a reducing agent.

9. The process of claim 4 wherein said material is a body fluid.

10. The process of claim 4 wherein said material is a colony of microorganisms.

11. The compound

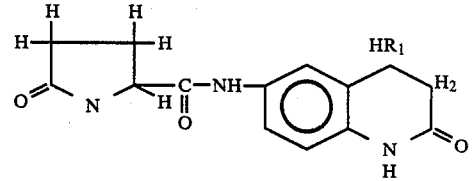

wherein R1 is selected from the group consisting of hydrogen and trifluoromethyl.

12. A dry article comprising

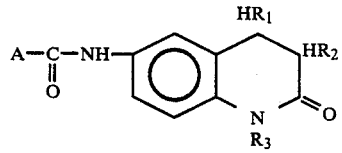

wherein A is an enzyme-specific substituent, R1, R2 and R3 are independently selected from the group consisting of hydrogen, an alkyl having fewer than five carbon atoms and a haloalkyl having fewer than five carbon atoms impregnated into an absorbent carrier from which all liquid is evaporated.

13. The article of claim 12 wherein said carrier is filter paper.

14. The article of claim 12 wherein said carrier is a porous mineral.

15. The article of claim 12 wherein said carrier is a porous polymer.

16. A dry article comprising

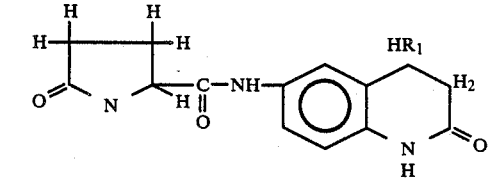

impregnated into an absorbent carrier from which all liquid is evaporated wherein R1 is a haloalkyl having fewer than five carbon atoms.

* * * * *

UNITED STATES PATENT AND TRADEMARK OFFICE
CERTIFICATE OF CORRECTION

PATENT NO. :  4,803,162
DATED      :  February 7, 1989
INVENTOR(S) :  Robert E. Smith, Eugene N. Fox It is certified that error appears in the above-identified patent and that said Letters Patent is hereby corrected as shown below:

Column 1, line 31, "of" should be --or--.
Column 1, line 32, "of" should be --or--.
Column 2, line 51, "of" should be --or--.
Column 2, line 61, "poous" should be -- porous--.
Column 3, line 63, "byleaving" should be --by leaving--.
Column 6, line 28, "tests" should be --test--.
Column 7, line 11, "isms" should be --ism--.

Signed and Sealed this

Twenty-fifth Day of July, 1989

*Attest:*

DONALD J. QUIGG

*Attesting Officer*         *Commissioner of Patents and Trademarks*